United States Patent
McConnell et al.

(10) Patent No.: US 7,115,718 B2
(45) Date of Patent: Oct. 3, 2006

(54) HAPTENS, IMMUNOGENS, ANTIBODIES AND CONJUGATES TO 2-OXO-3-HYDROXY-LSD

(75) Inventors: Robert Ivan McConnell, Ballymena (GB); Elouard Benchikh, Antrim (GB); Stephen Peter Fitzgerald, Crumlin (GB); John Victor Lamont, Crumlin (GB)

(73) Assignee: Randox :abpratproes :o, oted, Crumlin (GB)

( * ) Notice: Subject to any disclaimer, the term of this patent is extended or adjusted under 35 U.S.C. 154(b) by 362 days.

(21) Appl. No.: 10/326,771

(22) Filed: Dec. 20, 2002

(65) Prior Publication Data

US 2003/0143655 A1 Jul. 31, 2003

(30) Foreign Application Priority Data

Dec. 20, 2001 (EP) .................... 01205057

(51) Int. Cl.
| | | |
|---|---|---|
| C07K 16/00 | (2006.01) | |
| G01N 33/533 | (2006.01) | |
| G01N 33/534 | (2006.01) | |
| C07D 457/00 | (2006.01) | |
| C12N 9/96 | (2006.01) | |

(52) U.S. Cl. .............. 530/388.9; 530/389.8; 530/405; 436/545; 436/546; 436/814; 435/188; 546/69

(58) Field of Classification Search ............ 548/423; 530/405, 388.9, 389.8; 435/188; 436/545, 436/546, 815; 546/69

See application file for complete search history.

(56) References Cited

U.S. PATENT DOCUMENTS

| | | | | |
|---|---|---|---|---|
| 6,207,396 | B1 | 3/2001 | Sigler et al. | 435/7.6 |
| 6,306,616 | B1 * | 10/2001 | Shindelman | 435/7.93 |
| 6,794,496 | B1 * | 9/2004 | Ghoshal et al. | 530/405 |

FOREIGN PATENT DOCUMENTS

| | | |
|---|---|---|
| EP | 0 816 364 A1 | 1/1998 |
| EP | 1 148 339 A2 | 10/2001 |

OTHER PUBLICATIONS

Li, Z. et al., "New Synthesis and Characterization of (+)-Lysergic Acid Diethylamide (LSD) Derivatives and the Development of a Microparticle-Based Immunoassay for the Detection of LSD and Its Metabolites", XP 002175870, *Bioconjugate Chem.*, 1997, 8, 896-905.

Ratcliffe, W.A. et al., "Radioimmunoassay of Lysergic Acid Diethylamide (LSD) in Serum and Urine by Using Antisera of Different Specificities", *Clinical Chemistry*, XP 002041570, 1977, 23(2), 169-174.

* cited by examiner

*Primary Examiner*—Long V. Le
*Assistant Examiner*—Shafiqul Haq
(74) *Attorney, Agent, or Firm*—Woodcock Washburn LLP

(57) ABSTRACT

The invention provides a hapten derivatized with a crosslinker at the nitrogen of the 8β-carboxamide of 2-oxo-3-hydroxy LSD. The invention also provides an immunogen comprising the aforementioned hapten coupled to an antigenicity-conferring carrier material; a conjugate comprising the aforementioned hapten coupled to a labelling agent, as well as, antibodies raised against the aforementioned immunogen and capable of binding with at least the 3-hydroxy-2-pyrrolidone structural epitope of 2-oxo-3-hydroxy LSD.

30 Claims, 13 Drawing Sheets

Figure-1. Structure of LSD and related compounds
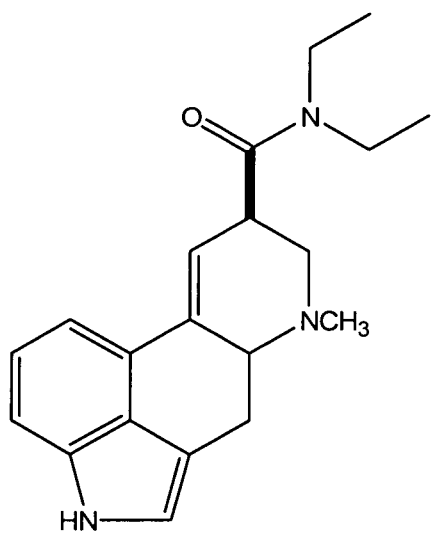
LSD 1
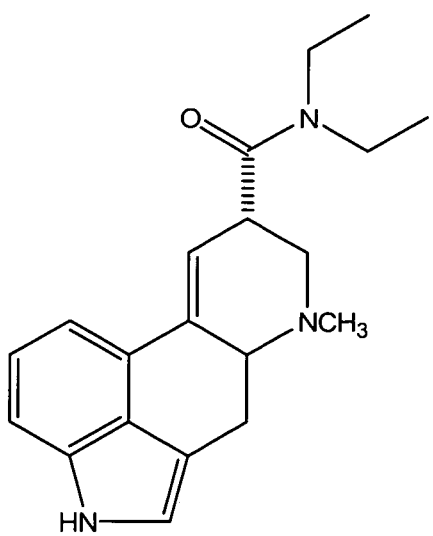
iso-LSD 2
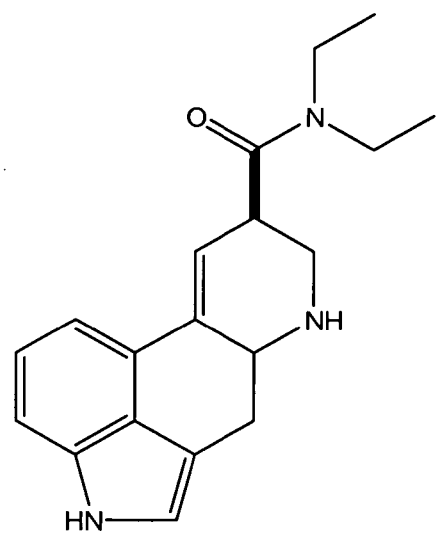
nor-LSD 3
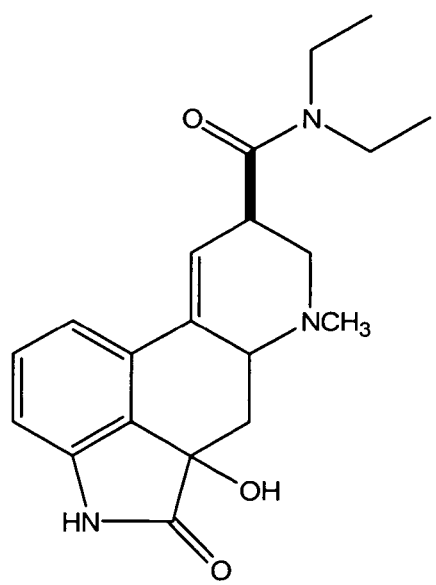
2-oxo-3-hydroxy-LSD 4

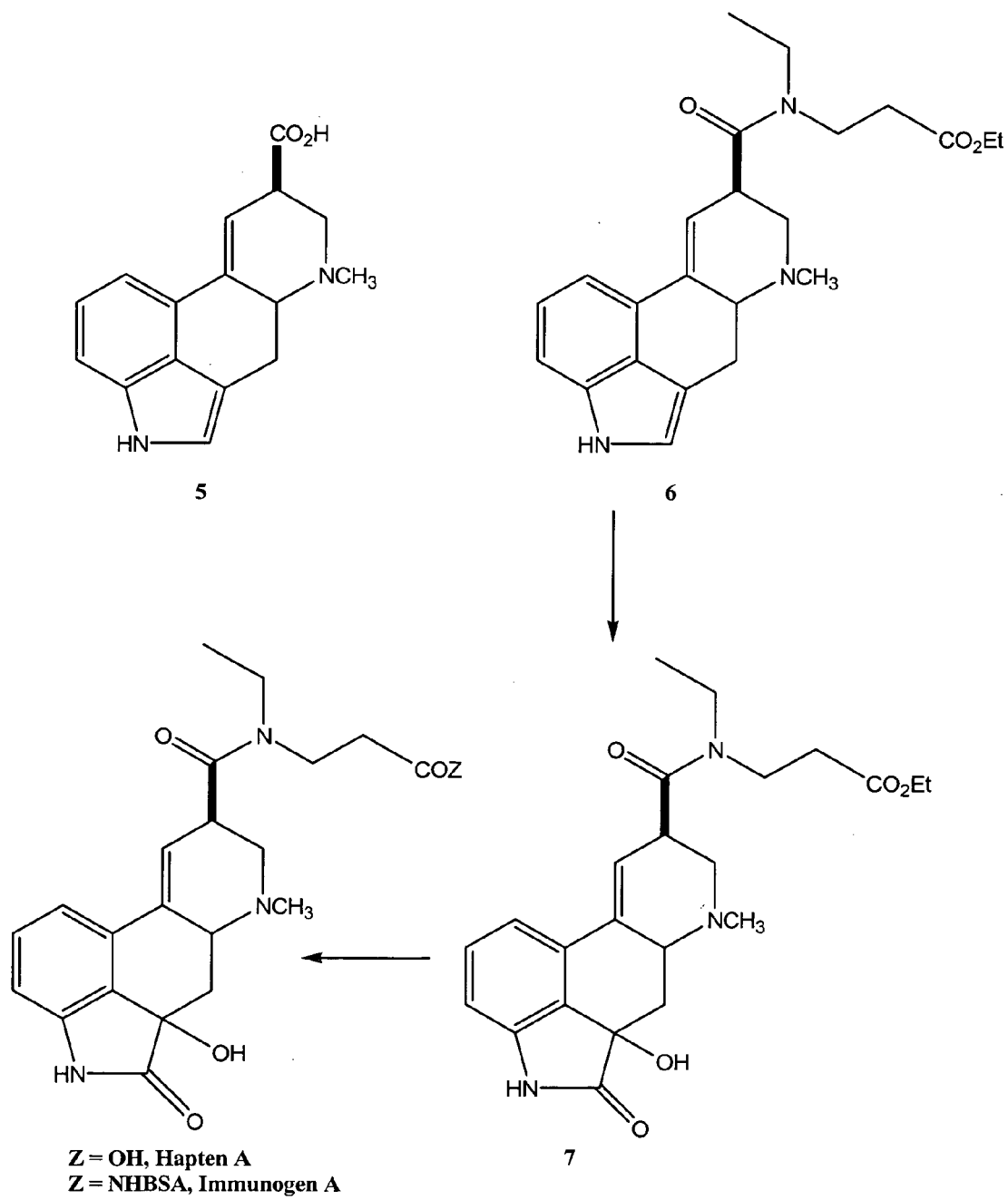
Figure-2. Hapten A and immunogen A for 2-oxo-3-hydroxy LSD

Figure-3: Hapten B and Immunogen B for 2-oxo-3-hydroxy LSD
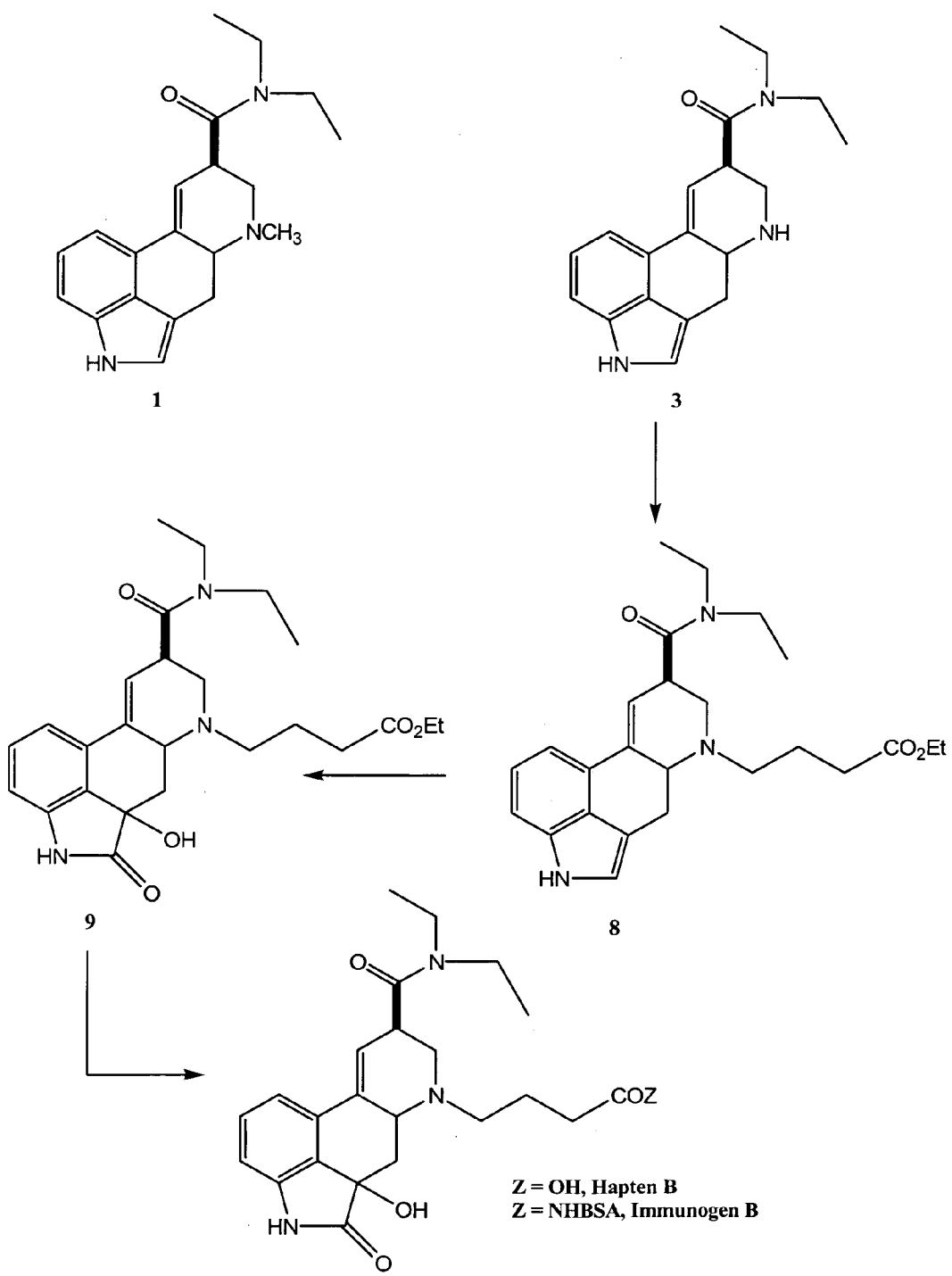

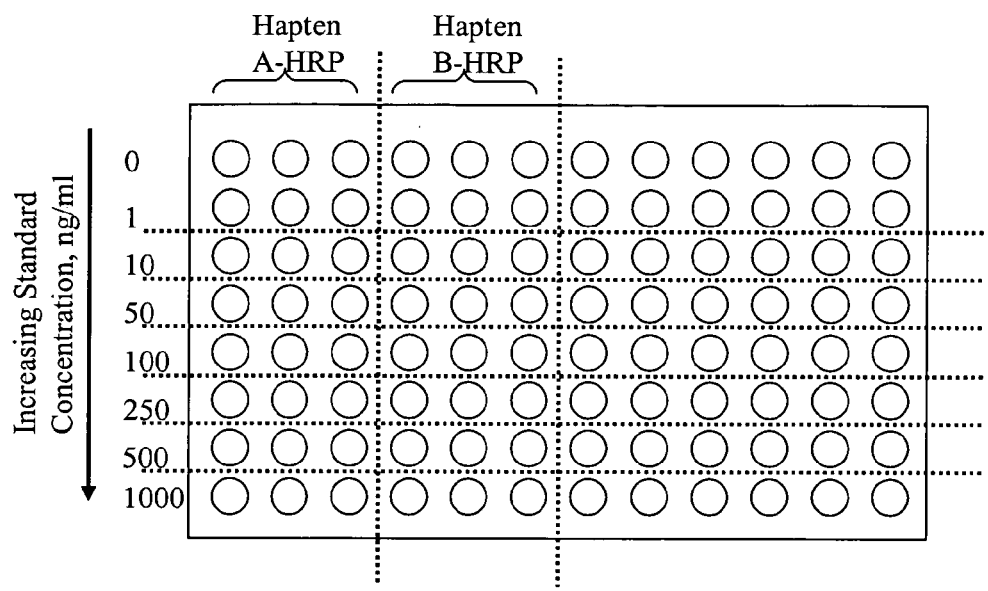
Figure-4: Competitive ELISA microtiter plate assays for 2-oxo-3-hydroxy-LSD

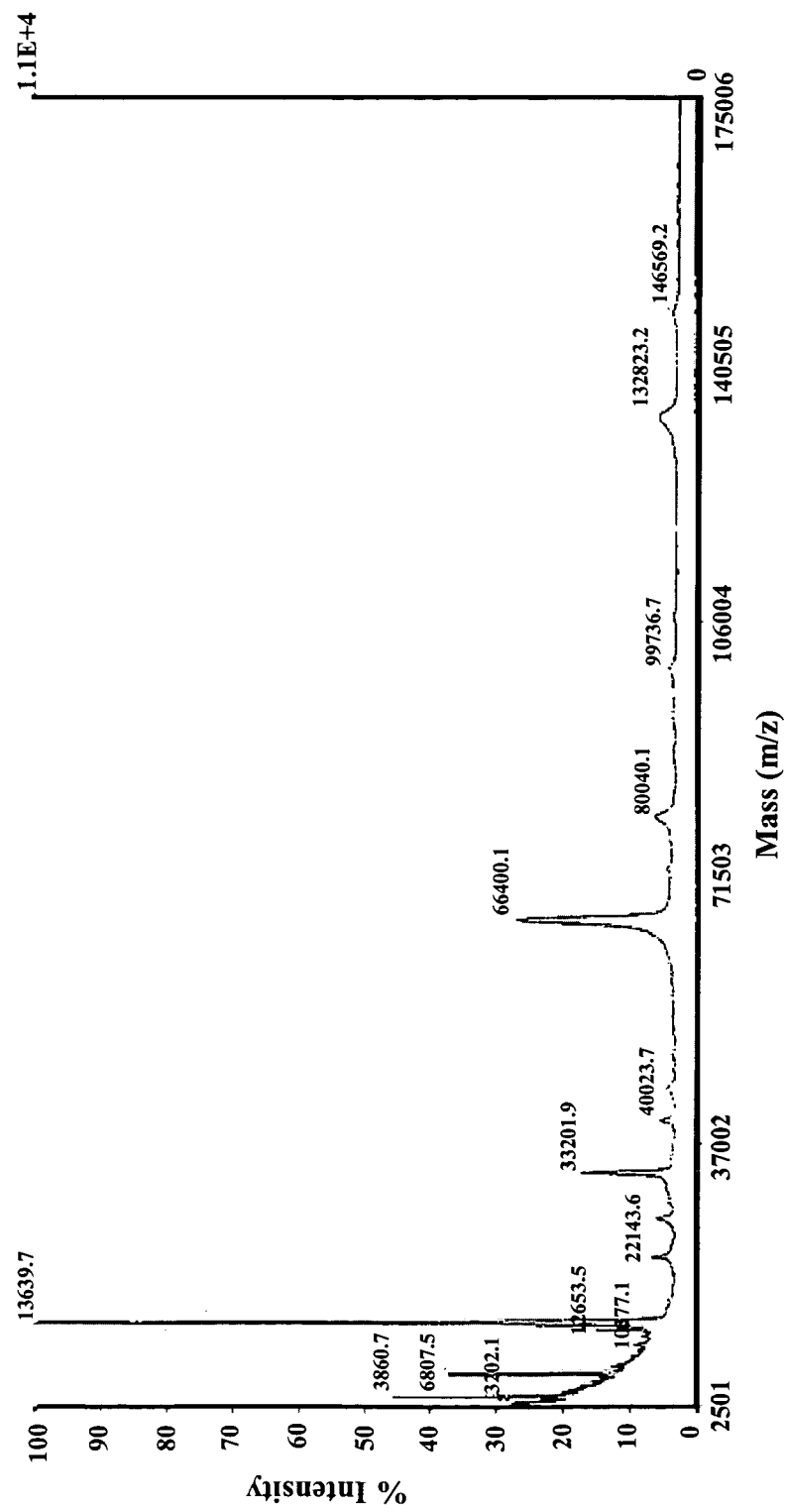
Figure 5: BSA Carrier Material

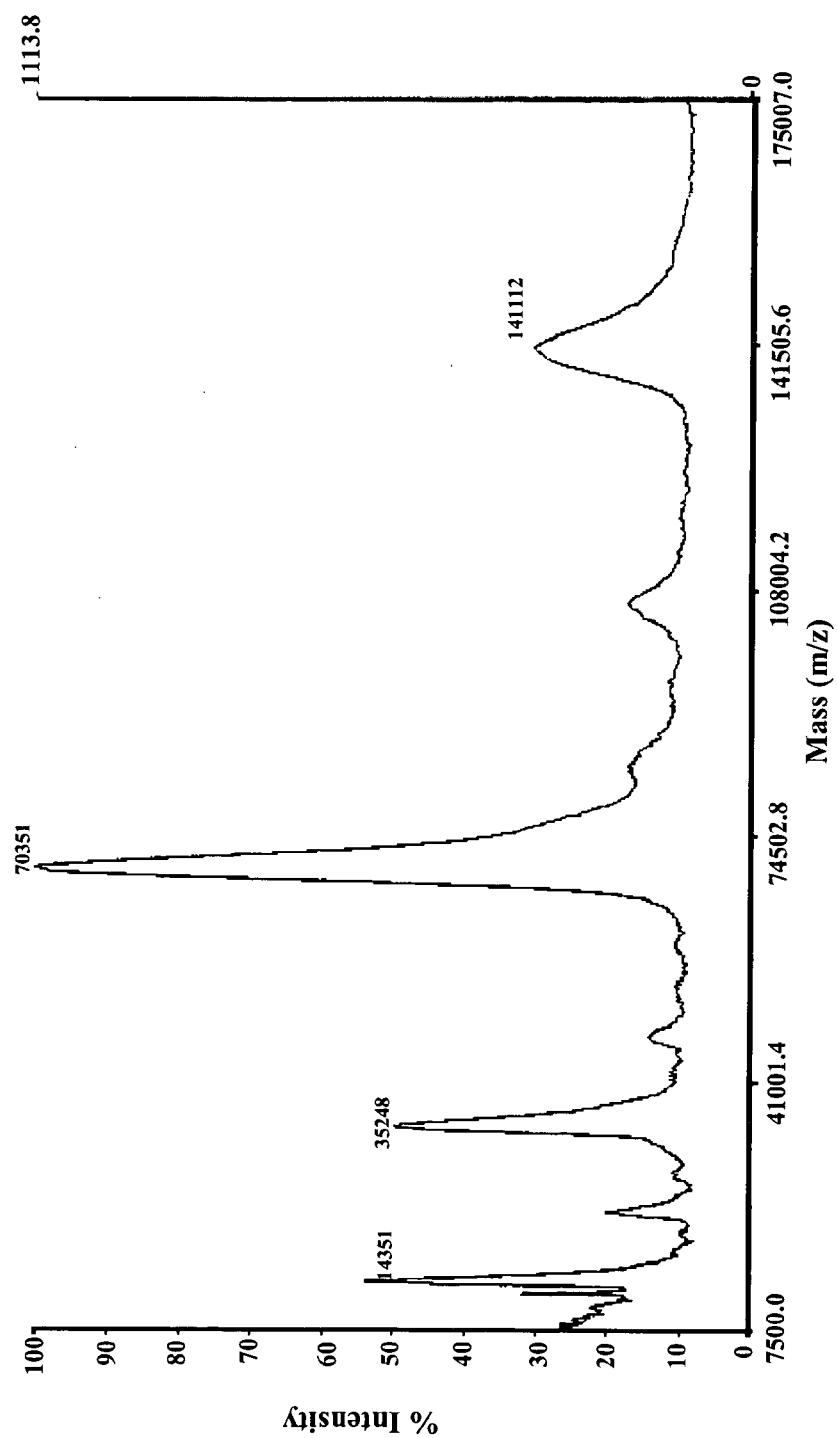
Figure 6: Immunogen A

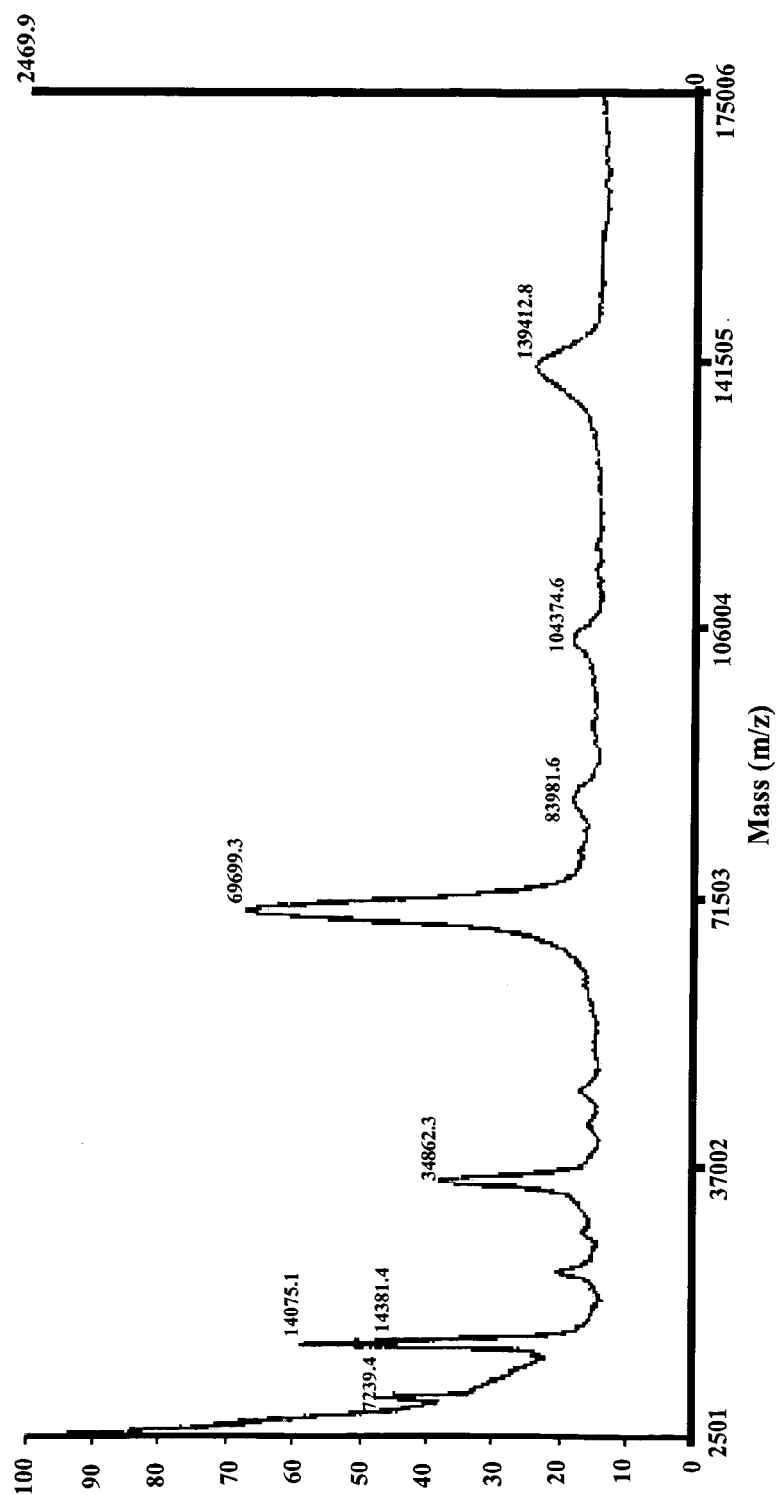
Figure 7: Immunogen B

HAPTENS, IMMUNOGENS, ANTIBODIES AND CONJUGATES TO 2-OXO-3-HYDROXY-LSD

BACKGROUND

The present invention relates to haptens that are used for the preparation of immunogens, antibodies and conjugates for use in competitive immunoassays for the detection of the major LSD metabolite, 2-oxo-3-hydroxy-LSD.

The present invention also relates to a method and kit for detecting or determining 2-oxo-3-hydroxy-LSD. The method and kit of the present invention are intended not to significantly cross-react with parent LSD itself or with nor LSD.

By "detecting" is meant qualitatively analysing for the presence or absence of a is substance.

By "determining" is meant quantitatively analysing for the amount of a substance.

Lysergic acid diethylamide (LSD) (FIG. 1, 1) is a powerful, psychoactive compound. It is classified as a Schedule I drug. The compound is available in pills, solutions and impregnated sugar cubes, blotting paper or vitamin tablets.

LSD is a very potent hallucinogen, 10–150 times as potent as psilocybin and 4500–9275 times as potent as mescaline. The isomeric compound d-iso-LSD (FIG. 1, 2) is inactive.

With increasing restrictions on administration of LSD to human subjects, current knowledge on the distribution, metabolic profile and extraction of LSD in man is limited. A considerable number of reports are available on the distribution and metabolic profile of LSD in animals where the most common metabolites found are nor-LSD (FIG. 1, 3), 2-oxo-3-hydroxy-LSD (FIG. 1, 4), 2-oxo-LSD, 13-hydroxy-LSD, 14-hydroxy-LSD, N-desethyl-LSD, N-ethyl-N-(2-hydroxyethyl)-LSD (amide N), N-ethyl-N-vinyl-LSD (amide N) and lysergic acid. The major metabolites are nor-LSD 3 and 2-oxo-3-hydroxy LSD 4, the latter of which was only recently detected in human urine submitted for drug testing, its identity having been confirmed by comparing LC-MS characteristics with a reference compound. The average concentration of 2-oxo-3-hydroxy-LSD 4 was 20 times more than that of LSD. In routine analysis of human urine, d-iso-LSD 2 was also detected. This compound is believed to be a by-product from the illicit preparation of LSD.

Due to the very low dose consumed (usually 40 to 120 µg) and due to rapid metabolism with less than 1% excreted unchanged in urine, identification of LSD in biological samples is a major challenge to forensic scientists. Furthermore, the instability of LSD in acid, heat and light has made its identification even more challenging. Because LSD is metabolized to a number of compounds, most known methods are aimed at identifying unchanged (or parent) LSD in biological samples.

Although LSD is most commonly detected in urine by GC-MS, immunoassays, particularly competitive binding immunoassays, would be the simplest and most time-saving screening methods available. Competitive binding immunoassays, as their name implies, measure competition in binding to antibody between a fixed amount of labeled antigen, the 'detection reagent' (or conjugate), and an unknown quantity of unlabelled antigen, the 'sample'.

Commercial immunoassay methods for LSD include radioimmunoassay procedures which are very sensitive, but do require radionuclide tracers, for example $^{125}$I and $^3$H, and, in some cases, a preliminary extraction step. For urine drug testing by radioimmunoassay, samples are identified as positive or negative by comparing the counts with that of a cut-off standard containing 500 pg/ml of LSD.

Nonisotopic homogeneous immunoassays for LSD are also commercially available. The Cloned Enzyme Donor Immunoassay (CEDIA, Boehringer Mannheim) and Enzyme Multiplied Inmunoassay (EMIT, Behring Diagnostics) are based on the principle of enzyme activation. The Online Immunoassay (Roche Diagnostic Systems) is based on kinetic interaction of microparticles in solution. These three assays are specially designed for large-scale analysis or automated analyzers. Microplate Immunoassay (STC Diagnostics) is available for small-scale testing. These nonisotopic LSD immunoassays correlate well with the original LSD radioimmunoassays.

All currently commercially available LSD immunoassay methods are specific for the parent drug, LSD, and generally exhibit low cross-reactivity with LSD metabolites.

For example, U.S. Pat. No. 6,207,396 B1 (Microgenics Corporation) discloses haptens that are derivatives of the LSD parent drug (not 2-oxo-3-hydroxy LSD), through the indole ring N-1 position. The antibodies of U.S. Pat. No. 6,207,396 B1 are specific to d-LSD and do not cross-react well with 2-oxo-3-hydroxy-LSD (1.82%) or with iso-LSD (0.04%) (see Table 1).

Examination of the prior art fails to reveal an antibody specific for 2-oxo-3-hydroxy LSD. EP 1 148 339 A2 (Roche Diagnostics Corporation) discloses haptens derivatised at position N-1, either of the indole ring of 2-oxo-3-hydroxy-LSD or of 2-oxo-LSD. The antibodies obtained in EP 1 148 339 A2 displayed high levels of cross-reactivity, when compared to 2-oxo-3-hydroxy-LSD, to the parent drug LSD (74.9–84.4%) and low cross-reactivity to the second metabolite, nor-LSD (1.8–4.6%) (paragraph 71).

EP 0 816 364 A1 (F. Hoffmann-La-Roche AG) and Bioconjugate Chemistry 1997, 8, pp 896–905 each describe the preparation of haptens either at the N-1 position of the indole ring of LSD itself or from nor LSD. Bioconjugate Chemistry 1997, 8, 896–905 discloses that antibodies generated to immunogen 4 displayed 100% cross-reactivity with d-LSD, 20% cross-reactivity with nor-LSD and 50% cross-reactivity with 2-oxo-3-hydroxy-LSD. Antibodies generated to immunogen 8 displayed 100% cross-reactivity with LSD, 40% cross-reactivity with nor-LSD and <20% cross-reactivity with 2-oxo-3-hydroxy-LSD.

Clin. Chem. 23/2, 169–174 (1977) describes a radioimmunoassay for LSD in serum and urine, employing antisera to two different immunogens, in which LSD itself is derivatised either at the indole nitrogen atom or via the nitrogen of the 8β-carboxamide.

The present inventors are unaware of any haptens derivatised with a crosslinker at the nitrogen of the 8β-carboxamide of 2-oxo-3-hydroxy-LSD.

The present inventors are also unaware of antibodies specific for 2-oxo-3-hydroxy-LSD but lacking significant cross-reactivity to parent LSD itself or to nor LSD.

SUMMARY OF THE INVENTION

The present invention provides a hapten derivatized with a crosslinker at the nitrogen of the 8β-carboxamide of 2-oxo-3-hydroxy-LSD.

The present invention also provides an immunogen comprising the aforementioned hapten, coupled to an antigenicity-conferring carrier material, as well as, conjugates comprising the aforementioned hapten covalently bonded to a detectable labelling agent. In addition, the present invention concerns antibodies raised against the aforementioned immunogens.

Finally, the present invention relates to methods and kits for detecting or determining 2-oxo-3-hydroxy-LSD in biological fluids.

The antibodies of the present invention are highly specific for 2-oxo-3-hydroxy-LSD but do not significantly cross-react with LSD or with nor LSD.

OBJECTS OF THE INVENTION

It is an object of the invention to overcome some or all of the disadvantages of the prior art, or to provide an alternative thereto.

It is an object of a preferred embodiment of the invention to provide a method and a kit for detecting, or determining the quantity of, 2-oxo-3-hydroxy-LSD.

The aim of the present invention is to overcome the lack of specificity problems associated with known immunoassays for LSD metabolites, by preparing a highly specific antibody to 2-oxo-3-hydroxy-LSD, which will not significantly cross-react with parent LSD or with nor LSD. By "not significantly" is meant a cross-reactivity of less than about 25%, preferably less than about 10%, more preferably less than about 7.5%, still more preferably less than about 5% when compared to 100% for 2-oxo-3-hydroxy-LSD. In order to achieve such specificity, the haptens described in the present invention are generated by derivatisation at the nitrogen of the 8β-carboxamide of 2-oxo-3-hydroxy-LSD.

It is a further object of a preferred embodiment of the present invention to develop antibodies capable of binding with at least the 3-hydroxy-2-pyrrolidone structural epitope of 2-oxo-3-hydroxy-LSD.

BRIEF DESCRIPTION OF THE DRAWINGS

FIG. 1 shows the chemical formulae for lysergic acid diethylamide (LSD) (1); d-iso-LSD (2); nor-LSD (3); and 2-oxo-3-hydroxy-LSD (4).

FIG. 2 shows preparation of Hapten A and Immunogen A in three steps from lysergic acid (5). Intermediates shown are lysergic acid N-ethyl N-(2-carbethoxy)ethyl amide, (6); and 2-oxo-3-hydroxy lysergic acid N-ethyl N-(2-carbethoxy)ethyl amide (7).

FIG. 3 shows preparation of Hapten B and Immunogen B in three steps from nor-LSD (3). Also shown are starting material, LSD (1); and intermediates 6-(3-carboethoxy)propyl-nor-LSD (8) and 2-oxo-3-hydroxy-6-(3-carboethoxy)propyl-nor-LSD (9).

FIG. 4 shows a diagram of an ELISA plate for a competitive ELISA assay for 2-oxo-3-hydroxy-LSD.

FIG. 5 shows MALDI-TOF mass spectrometry for BSA carrier performed using a Voyager STR Biospectrometry Research Station laser-desorption mass spectrometer coupled with delayed extraction.

FIG. 6 shows MALDI-TOF mass spectrometry for Immunogen A performed using a Voyager STR Biospectrometry Research Station laser-desorption mass spectrometer coupled with delayed extraction.

FIG. 7 shows shows MALDI-TOF mass spectrometry for Immunogen B performed using a Voyager STR Biospectrometry Research Station laser-desorption mass spectrometer coupled with delayed extraction.

DETAILED DESCRIPTION OF INVENTION

Figure 8:
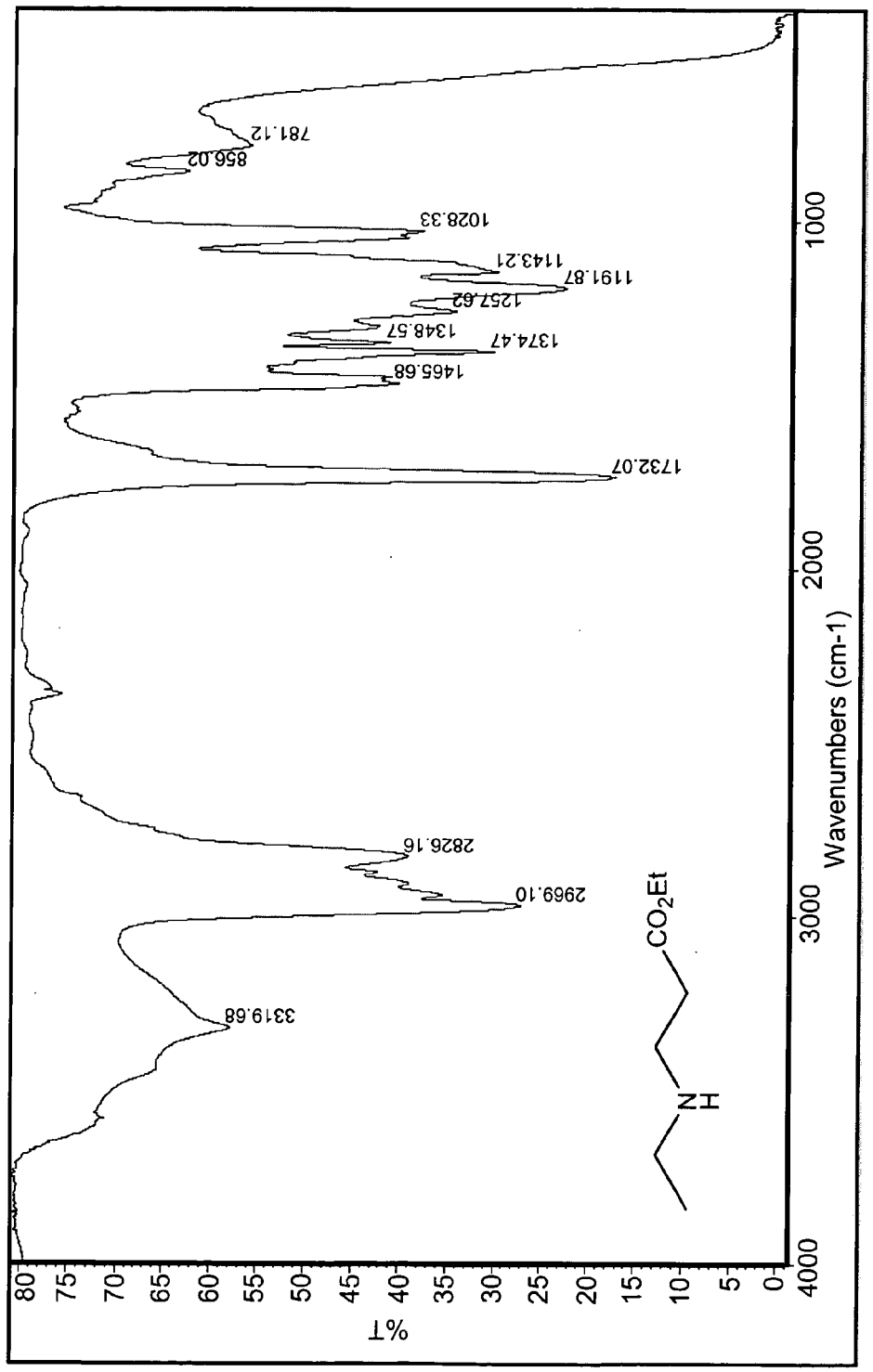
FIG. 8 shows an FT-IR scan of the N-ethyl N-(2-carbethoxy)ethyl amine linker (10).

The present invention describes a hapten derivatised with a crosslinker, either at the nitrogen of the 8β-carboxamide or at N-6, of 2-oxo-3-hydroxy-LSD (FIG. 1, 4).

In a first aspect, the present invention provides a hapten of the following structural formula:-

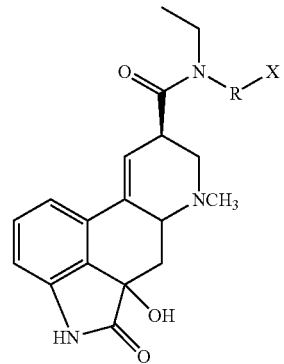

in which R is a bivalent link and X is a terminal group.

Preferably, R comprises a substituted or unsubstituted, straight or branched chain, saturated or unsaturated, alkylene moiety, a substituted or unsubstituted, saturated or unsaturated, cycloalkylene moiety or a substituted or unsubstituted arylene moiety; and X independently comprises a carboxylic acid or an ester thereof, an aldehyde, a thiocarboxylic acid or an ester thereof, preferably thioacetyl, or a halocarboxylic acid or an ester thereof, preferably haloacetyl.

Thus, in the above-mentioned structural formula, the crosslinker comprises —R—X.

More preferably, R is a $C_{1-6}$, most preferably a $C_{2-3}$, substituted or unsubstituted, straight chain, saturated alkylene moiety.

Suitable cycloalkylene moieties include cyclohexane.

Suitable arylene moieties include benzene and xylene.

Advantageously, X is carboxylic acid.

Most preferably, the hapten is the following hapten derivative of 2-oxo-3-hydroxy-LSD:

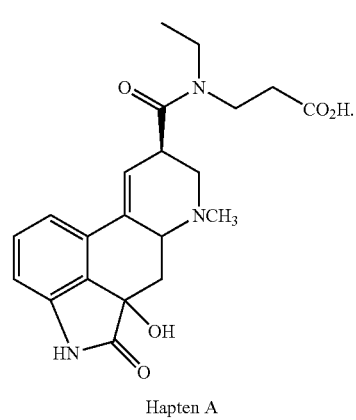

Hapten A

In Hapten A of the present invention, R is a saturated, unsubstituted straight chain alkylene group having 2 carbon atoms. In Hapten B, which is described herein, R is a saturated, unsubstituted, straight chain alkylene group having 3 carbon atoms.

The terminal groups X are used for coupling the haptens of the present invention to carrier materials for the preparation of the corresponding immunogens. The resulting immunogens can be administered to hosts to elicit production of avid specific antisera, preferably polyclonal antisera, which are then used to develop sensitive immunoassays for the detection of 2-oxo-3-hydroxy-LSD.

The invention, therefore, also provides an immunogen comprising a hapten according to the present invention, coupled to an antigenicity-conferring carrier material. Preferably, the carrier material is a protein, a protein fragment, a synthetic polypeptide or a semi-synthetic polypeptide.

In a further aspect, the present invention concerns antibodies raised against the immunogen of the present invention, the antibodies being capable of binding with at least the 3-hydroxy-2-pyrrolidone structural epitope of 2-oxo-3-hydroxy-LSD. Preferably, the antibodies are fixed on a backing substrate. Preferably, the antibodies are polyclonal. Alternatively, the antibodies are monoclonal.

In a still further aspect, the present invention comprises a conjugate comprising the hapten of the present invention covalently bonded to a detectable labelling agent. Preferably, the labelling agent is selected from an enzyme, a luminescent substance, a radioactive substance, or a mixture thereof. More preferably, the labelling agent is an enzyme, preferably a peroxidase, most preferably horseradish peroxidase (HRP). Alternatively, or additionally, the luminescent substance may be a bioluminescent, chemiluminescent or fluorescent material.

The invention further provides a process of preparing the antibodies, the process comprising the steps of immunising an animal, preferably a vertebrate animal, most preferably a mammalian animal, by repeated administration of an immunogen according to the present invention, and collecting the resulting serum from the immunised animal. Preferably, the process further comprises fixing said serum antibodies to a backing substrate, preferably a solid support, most preferably a polystyrene solid support. Antibodies prepared in accordance with this process are polyclonal.

In a further aspect, the present invention comprises a method for detecting or determining 2-oxo-3-hydroxy-LSD in a sample, the method comprising contacting the sample with the conjugate of the present invention, or a mixture thereof, and with antibodies of the present invention, or a mixture thereof; detecting or determining bound conjugate; and deducing from a calibration curve the presence of, or the amount of, 2–6xo-3-hydroxy-LSD in the sample.

In a still further aspect, the invention includes a kit for detecting or determining 2-oxo-3-hydroxy-LSD, the kit including the conjugate of the present invention, or a mixture thereof; and the antibodies of the present invention, or a mixture thereof. The kit may optionally include instructions for the use of said conjugates and said antibodies for detecting or determining 2-oxo-3-hydroxy-LSD in a sample.

Preferably, the sample is a solution, such as a biological fluid. More preferably, the sample is serum or urine. Most preferably, the sample is a solution from a human patient.

In the method and kit of the present invention, it is preferred that the respective crosslinkers (of the immunogen and the conjugate) are different.

In a further aspect, the present invention involves use of the conjugates according to the present invention, or a mixture thereof, with the antibodies according to the present invention, or a mixture thereof, to detect or determine 2-oxo-3-hydroxy-LSD in samples such as biological fluids.

The focus of the present invention is the preparation of antibodies specific to 2-oxo-3-hydroxy-LSD (FIG. 1, 4). In order to achieve such specificity, hapten A is generated by derivatization of 2-oxo-3-hydroxy-LSD at the N-carboxamide.

Preparation of Haptens

Hapten A of the present invention was prepared in three steps from lysergic acid (see FIG. 2 of the accompanying drawings). The carboxylic group of lysergic acid 5 was activated with 1,1'-carbonyldiimidazole (CDI) in dimethylformamide (DMF). The activated ester intermediate obtained was reacted with N-ethyl N-(2-carbethoxy)ethyl amine 10 (prepared by reaction of ethyl amine with ethyl acrylate) to yield ester 6. Oxidation of the double bond of the indole ring of the tartrate salt of ester 6 with calcium hypochlorite, generated in situ by the action of chlorine gas on calcium hydroxide, produced the ester 2-oxo-3-hydroxy lysergic acid N-ethyl N-(2-carbethoxy)ethyl amide 7. Hapten A was obtained after saponification of ester 7 by aqueous potassium hydroxide in tetrahydrofuran.

Hapten B, which is described herein, was prepared in three steps from nor-LSD 3 (see FIG. 3 of the accompanying drawings). N-alkylation of nor-LSD 3 with ethyl 4-bromobutyrate in the presence of sodium hydride in DMF produced ester 8. Oxidation of the double bond of the indole ring of ester 8 was performed using the same conditions used for oxidation of ester 6, to produce the ester 2-oxo-3-hydroxy-6-(3-carboethoxy)propyl-nor-LSD 9. Hapten B was obtained after saponification of 9 using aqueous potassium hydroxide in tetrahydrofuran.

Preparation of Immunogens and Conjugates

Although the haptens of the present invention provide defined structural epitopes, they are not in themselves immunogenic and therefore need to be conjugated to a carrier material, which will elicit an immunogenic response when administered to a host animal. Suitable carrier materials commonly contain poly(amino acid) segments and include polypeptides, proteins such as albumins, serum proteins e.g. globulins and ocular lens proteins and lipoproteins. Illustrative protein carrier materials include bovine serum albumin (BSA), egg ovalbumin, bovine gamma globulin, thyroxine binding globulin, keyhole limpet haemocyanin (KLH) etc. Alternatively, synthetic poly (amino acids) having a sufficient number of available amine groups such as lysine may be employed, as may other synthetic or natural polymeric materials bearing reactive functional groups. In particular, carbohydrates, yeasts or polysaccharides may be conjugated to the haptens of the present invention to produce immunogens of the present invention.

Each hapten of the present invention can also be coupled to a labelling agent such as an enzyme (for example, horse radish peroxidase), a substance having fluorescent properties or a radioactive label for the preparation of conjugates (or detection reagents) for use in the immunoassays. The fluorescent substance may be, for example, a monovalent residue of fluorescein or a derivative thereof.

In preparing immunogens or conjugates with haptens of the present invention where a thiol group is present, i.e., where X is a thiocarboxylic acid or an ester thereof, maleimide, halo or vinylsulphone groups must first be introduced to the carrier material or labelling agent (enzyme or label) using heterobifunctional linkers such as: N-(γ-maleimidobutyryloxy)succinimide ester (GMBS); succinimidyl 4-(N-maleimidomethyl)cyclohexane-1-carboxylate (SMCC); (m-maleimidobenzoyl)-N-hydroxysuccinimide (MBS); succinimidyl 4-(p-maleimidophenyl)butyrate (SMPB); N-succinimidyl(4-iodoacetyl)aminobenzoate (SIAB); bromoacetylglycine N-hydroxysuccinimide; N-succinimidyl 3-(2-pyridyldithio)propionate (SPDP); or vinylsulphone (Pierce Chemical Company, USA). The thus-modified carrier material or labelling agent can then be conjugated via the thiol groups on the hapten. For haptens without a thiol group present, such as hapten A of the present invention, conjugation is performed without prior-modification of the carrier material or labelling agent using standard methods of conjugation such as mixed anhydride, EDC or succinimidyl activation of the hapten.

In order to confirm that adequate conjugation of hapten to carrier material has been achieved, prior to immunization, each immunogen is evaluated using matrix-assisted UV laser desorption/ionization time-of-flight mass spectroscopy (MALDI-TOF MS). In the case of the preferred carrier material, bovine serum albumin, a minimum of 6 molecules of hapten per carrier molecule is preferred. Each of the immunogens of the present invention can be used for immunization, in order to produce antibodies of the present invention.

General Procedure for MALDI-TOF Analysis of Immunogens.

MALDI-TOF mass spectrometry was performed using a Voyager STR Biospectrometry Research Station laser-desorption mass spectrometer coupled with delayed extraction. An aliquot of each sample to be analysed was diluted in 0.1% aqueous trifluoroacetic acid (TFA) to create 1 mg/ml sample solutions. Aliquots (1 µl) were analysed using a matrix of Sinapinic acid and bovine serum albumin (Fluka) was used as an external calibrarit. FIG. 5 of the accompanying drawings shows the analysis for BSA carrier material. As will be seen, a major signal was present which indicates an average protonated mass for this sample of m/z 66,400. The signal at m/z 33,202 is consistent with the major component in a doubly-charged form.

Preparation of Antisera

In order to generate polyclonal antisera, each immunogen of the present invention is mixed with Freund's Adjuvant and the mixture is injected into a host animal, such as a rabbit, sheep, mouse, guinea pig or horse. Further injections (boosts) are made and serum is sampled for evaluation of antibody titer. When the optimal titer has been reached, the host animal is then bled to yield a suitable volume of specific antiserum. The degree of antibody purification required depends on the intended application. For many purposes, there is no requirement at all for purification, however, in other cases, such as where the antibody is to be immobilized on a solid support, purification steps can be taken to remove undesired material and eliminate non-specific binding.

The specific antibodies of the present invention are useful as reagents in biochemical assays for the detection or determination of 2-oxo-3-hydroxy-LSD in biological fluids.

In the following Examples, percentages are to be taken as percentages (volume/volume), unless otherwise specified.

EXAMPLES

Example 1

Synthesis of N-ethyl N-(2-carbethoxy)ethyl Amine Linker 10

To 110 ml of a 2M solution of ethyl amine in tetrahydrofuran (THF) at 0° C. was added dropwise ethyl acrylate (8.0 ml, 73.92 mmol) in 40 ml of tetrahydrofuran (THF). The reaction mixture was stirred overnight at room temperature. The reaction solution was filtered through a cotton wool plug and concentrated under reduced pressure to yield the title compound 10 (9.01 g, 84%) as a clear liquid.

$\upsilon_{max}/cm^{-1}$ 3319.68, 2969.10, 1732.07, 1191.87 (FT-IR: FIG. 8)

Example 2

Synthesis of Lysergic Acid N-ethyl N-(2-carbethoxy)ethyl Amide 6

A mixture of lysergic acid 5 (934 mg, 3.27 mmol) in 40 ml of dry dimethylformamide (DMF) was treated with 1,1'-carbonydidimidazole (CDI, 795 mg, 4.91 mmol) and stirred under nitrogen at room temperature for 1 hour. The N-ethyl N-(2-carbethoxy)ethyl amine linker 10 (1.90 g, 13.08 mmol) in 10 ml of dry dimethylformamide (DMF) was added dropwise and the reaction solution was stirred overnight at room temperature. The reaction solution was concentrated under reduced pressure and the resulting residue was dissolved in 200 ml of chloroform. The chloroform solution was washed twice with 100 ml of water, dried over anhydrous sodium sulphate, and concentrated under reduced pressure to yield the crude title compound 6 (2.2 g) as an oil. This was used without further purification in the following Example.

Figure 9:
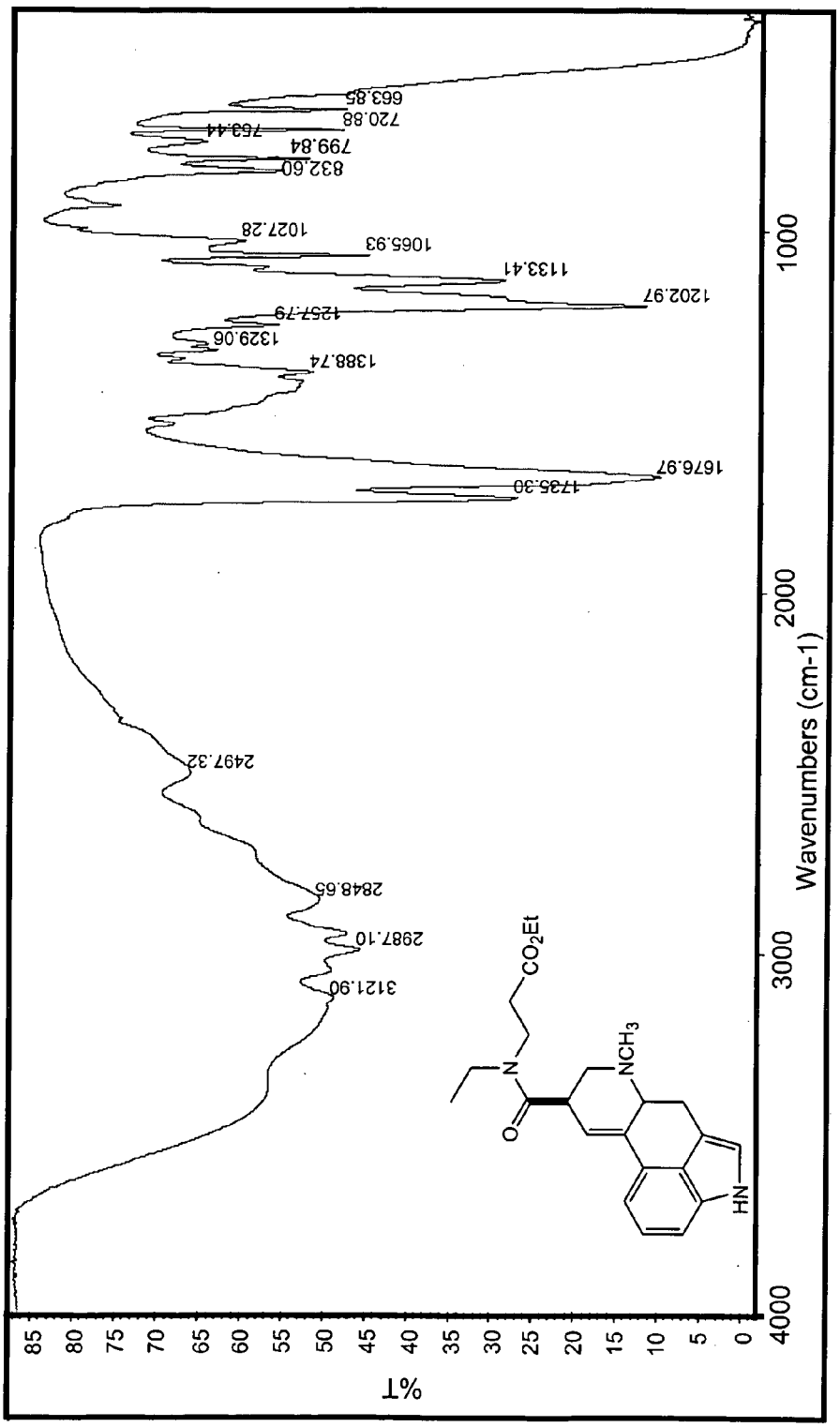
FIG. 9 shows an FT-IR scan of lysergic acid N-ethyl N-(2-carbethoxy)ethyl amide (6).

$\upsilon_{max}/cm^{-1}$ 3121.90, 2987.10, 2848.65, 1735.30, 1676.97, 1202.97 (FT-IR: FIG. 9)

Example 3

Synthesis of 2-oxo-3-hydroxy Lysergic Acid N-ethyl N-(2-carbethoxy)ethyl Amide 7

To a mixture of tartaric acid (2.52 g, 16.79 mmol) dissolved in 40 ml of water and cooled in ice, was added 2.2 g of crude lysergic acid N-ethyl N-(2-carbethoxy)ethyl amide 6 (1.29 g, 3.27 mmol; based on 100% yield from the previous Example). A solution of calcium hypochlorite was prepared by dissolving chlorine gas (1.55 g, 21.83 mmol) into a solution of calcium hydroxide (0.81 g, 10.93 mmol) in 240 ml of water. The cloudy solution was passed through a 0.45 µM membrane filter, to remove any undissolved material, and cooled in ice. To 170 ml of this freshly prepared calcium hypochlorite solution was added the lysergic acid N-ethyl N-(2-carbethoxy)ethyl amide tartrate solution. The reaction was stirred at 0° C.–5° C. for 30 min. The reaction mixture was diluted with 80 ml of saturated sodium bicarbonate solution and extracted with 6×100 ml of chloroform. The chloroform extracts were combined, dried over anhydrous sodium sulphate, and concentrated under reduced pressure. The resulting residue was chromatographed on silica gel to give 2-oxo-3-hydroxy lysergic acid N-ethyl N-(2-carbethoxy)ethyl amide 7 (385 mg, 28%) as an amorphous dark brown solid ($R_f$ 0.53 on silica using 25% methanol in chloroform as eluent).

Figure 10:
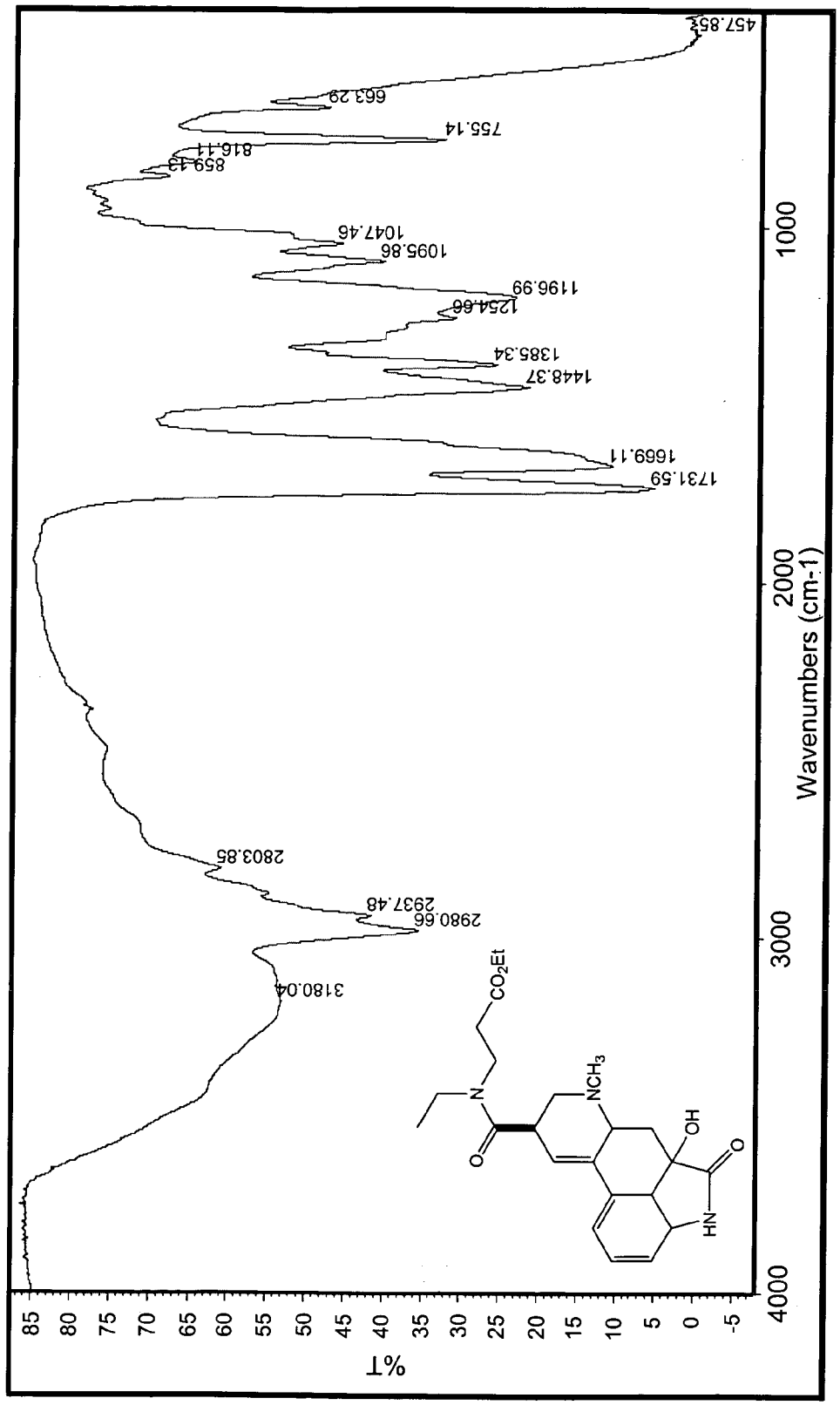
FIG. 10 shows an FT-IR scan of 2-oxo-3-hydroxy lysergic acid N-ethyl N-(2-carbethoxy)ethyl amide (7).

$\upsilon_{max}/cm^{-1}$ 3180.04, 2980.66, 2937.48, 2803.85, 1731.59, 1669.11, 1448.37, 1385.34 (FT-IR: FIG. 10)

Example 4

Synthesis of 2-oxo-3-hydroxy Lysergic Acid N-ethyl N-(2-carboxy)ethyl Amide (Hapten A)

To a mixture of 2-oxo-3-hydroxy lysergic acid Nethyl N-(2-carbethoxy)ethyl amide 7 (63.6 mg, 0.15 mmol) in 5 ml of tetrahydrofuran (THF) and 5 ml of water was added solid potassium hydroxide (12.5 mg, 0.22 mmol). The reaction was stirred at room temperature for 3 hours (h) until the reaction was complete by TLC analysis. The reaction solution was neutralised to pH 7 using 1N HCl and concentrated to dryness under reduced pressure. The residue was dissolved in a 10% methanol in chloroform mixture and the inorganic salts were removed by filtration. Evaporation of the solvents yielded 2-oxo-3-hydroxy lysergic acid N-ethyl N-(2-carboxy)ethyl amide (Hapten A) (45 mg, 76%) as an amorphous brown solid ($R_f$ 0.52 on silica using 20% methanol in chloroform as eluent).

$\upsilon_{max}$/cm$^{-1}$ 3297, 2963, 1723, 1557, 1099, 1026, 802 (FT-IR)

Example 5

Conjugation of 2-oxo-3-hydroxy Lysergic Acid N-ethyl N-(2-carboxy)ethyl Amide to BSA (Immunogen A)

To a solution of 2-oxo-3-hydroxy lysergic acid N-ethyl N-(2-carboxy)ethyl amide (Hapten A), (45 mg, 0.11 mmol) in 1 ml of dimethylforamide (DMF) was added dicyclohexylcarbodiimide (DCC) (27.9 mg, 0.14 mmol) and N-hydroxysuccinimide (NHS) (15.6 mg, 0.14 mmol) and the mixture was stirred at room temperature overnight. The dicyclohexylurea formed was filtered off and the solution was added dropwise to a solution of BSA (150 mg) in 6 ml of 0.05M sodium bicarbonate solution (pH 8.5). The mixture was stirred overnight at 4° C., protected from light. The solution was then dialysed overnight against 5 L of PBS (pH 7.2) at 4° C. and freeze-dried.

By MALDI-TOF (see FIG. 6 of the accompanying drawings), a major signal was present which indicates an average protonated mass for this sample of m/z 70,351. The signal at m/z 35,248 is consistent with the major component in a doubly-charged form. These data suggest that an average of 9.8 molecules of Hapten A have been conjugated per molecule of BSA.

Example 6

Synthesis of 6-cyano-nor-LSD

To a refluxing solution of cyanogen bromide (2.96 g, 27.95 mmol) in 150 ml of dry chloroform, under nitrogen, was added dropwise a solution of lysergic acid diethylamide 1 (2.00 g, 6.19 mmol) in 100 ml of dry chloroform. The reaction was heated under reflux for 4 hours and cooled to room temperature. The organic phase was extracted twice with 150 ml of a 1% (w/v) tartaric acid solution. The combined aqueous washes were extracted with 100 ml of chloroform and the combined organic phases were dried over anhydrous sodium sulphate, and concentrated under reduced pressure. The black residue was chromatographed on silica gel using ethyl acetate to yield 6-cyano-nor-LSD (879 mg, 42%) as a pale yellow solid after evaporation of the solvent.

$\upsilon_{max}$/cm$^{-1}$ 3192, 2933, 2212, 1636, 1449, 986

Example 7

Synthesis of nor-LSD 3

A mixture of 6-cyano-nor-LSD (879 mg, 2.63 mmol) in 8 ml of acetic acid and 2 ml of water, under nitrogen, was treated with zinc dust (1.53 g, 23.39 mmol) and heated under reflux for 6 h. The solution was allowed to cool and decanted off from the excess zinc with a water wash. The reaction solution was concentrated to a small volume under reduced pressure and the concentrate was diluted with 10 ml of water. The pH of the solution was taken to pH 9 using concentrated ammonia solution at 0° C. The resulting gummy precipitate was extracted four times with 50 ml of chloroform. The combined chloroform extracts were dried over anhydrous sodium sulphate and concentrated under reduced pressure to yield nor-LSD 3 (625 mg, 77%) as a light brown amorphous solid ($R_f$ 0.47 on silica using 20% methanol in chloroform as eluent).

$\upsilon_{max}$/cm$^{-1}$ 3260, 2974, 2934, 1620, 1447

Example 8

Synthesis of 6-(3-carboethoxy)propyl-nor-LSD 8

A mixture of nor-LSD 3 (625 mg, 2.02 mmol) in 5 ml of dry dimethyl formamide (DMF), was treated with ethyl bromobutyrate (290 μL, 2.02 mmol), potassium carbonate (839 mg, 6.06 mmol) and a catalytic amount of potassium iodide, and stirred under nitrogen at 40° C. overnight. The reaction solution was concentrated to a residue under reduced pressure and chromatographed on silica gel using 5% methanol in chloroform to yield 6-(3-carboethoxy)propyl-nor-LSD 8 (368 mg, 43%) after evaporation of the solvents ($R_f$ 0.77 on silica using 20% methanol in chloroform as eluent).

Figure 11:
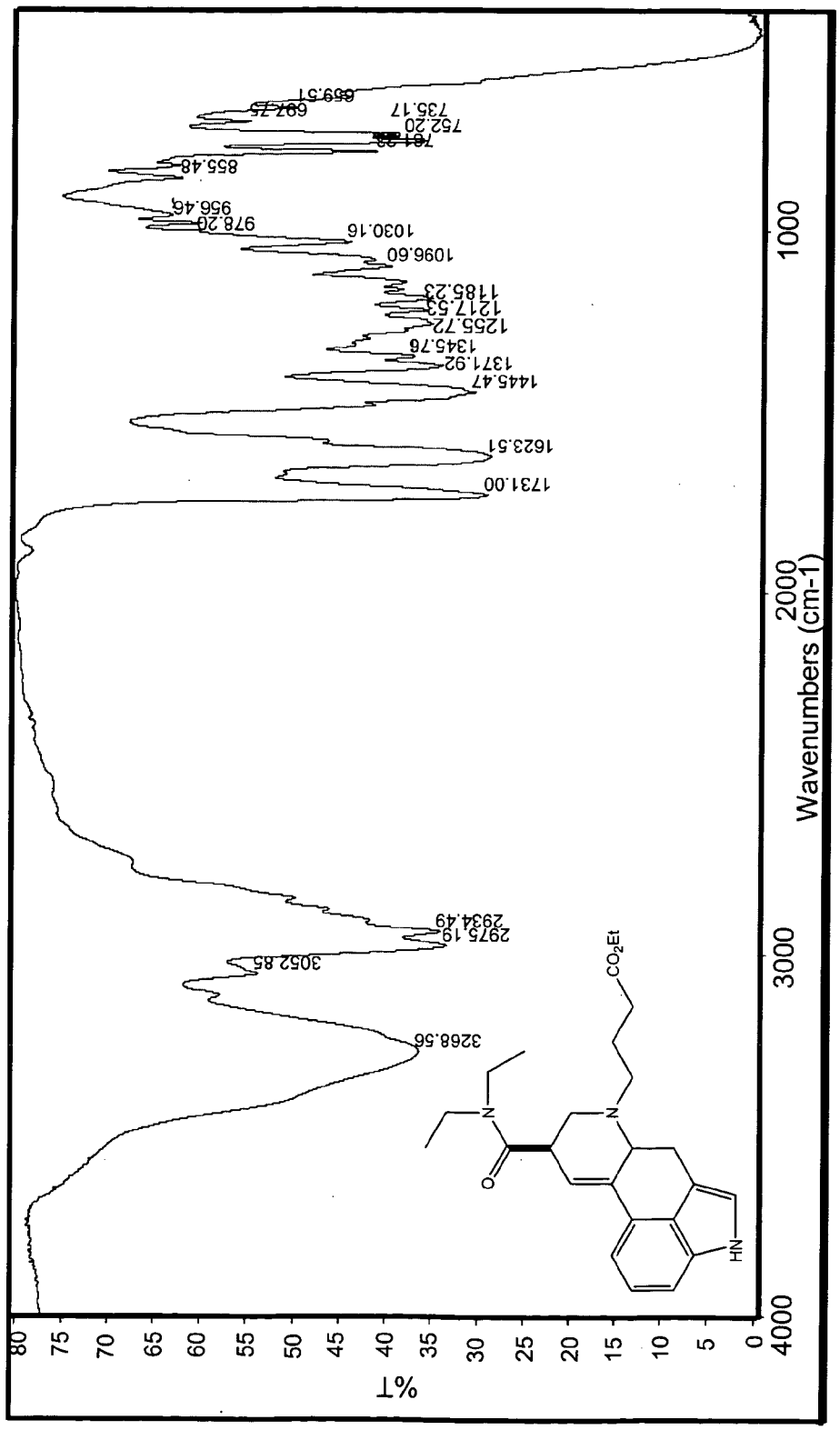
FIG. 11 shows an FT-IR scan of 6-(3-carboethoxy)propyl-nor-LSD (8).

$\upsilon_{max}$/cm$^{-1}$ 3268.56, 2975.19, 2934.49, 1731.00, 1623.51 (FT-IR : FIG. 11)

Example 9

Synthesis of 2-oxo-3-hydroxy-6-(3-carboethoxy)propyl-nor-LSD

To a mixture of tartaric acid (196 mg, 1.31 mmol) dissolved in 20 ml of water, cooled in ice, was added 6-(3-carboethoxy)propyl-nor-LSD 8 (368 mg, 0.87 mmol). A calcium hypochlorite solution was prepared by dissolving chlorine gas (1.55 g, 21.83 mmol) into a solution of calcium hydroxide (0.81 g, 10.93 mmol) in 240 ml of water. The cloudy solution was passed through a 0.45 μM membrane filter, to remove any undissolved material, and cooled in ice. To 45 ml of the freshly prepared calcium hypochlorite solution was added the 6-carboethoxypropyl-lysergic acid diethylamide tartrate solution and the reaction was stirred at 0° C.–5° C. for 30 min. The reaction was diluted with 80 ml of saturated sodium bicarbonate solution and extracted with 6×100 ml of chloroform. The chloroform extracts were combined, dried over anhydrous sodium sulphate, and concentrated under reduced pressure. The resulting residue was chromatographed on silica gel to give 2-oxo-3-hydroxy-6-(3-carboethoxy)propyl-nor-LSD 9 (102 mg, 26%) as a brown solid ($R_f$ 0.44 on silica using 10% methanol in chloroform as eluent).

Figure 12:
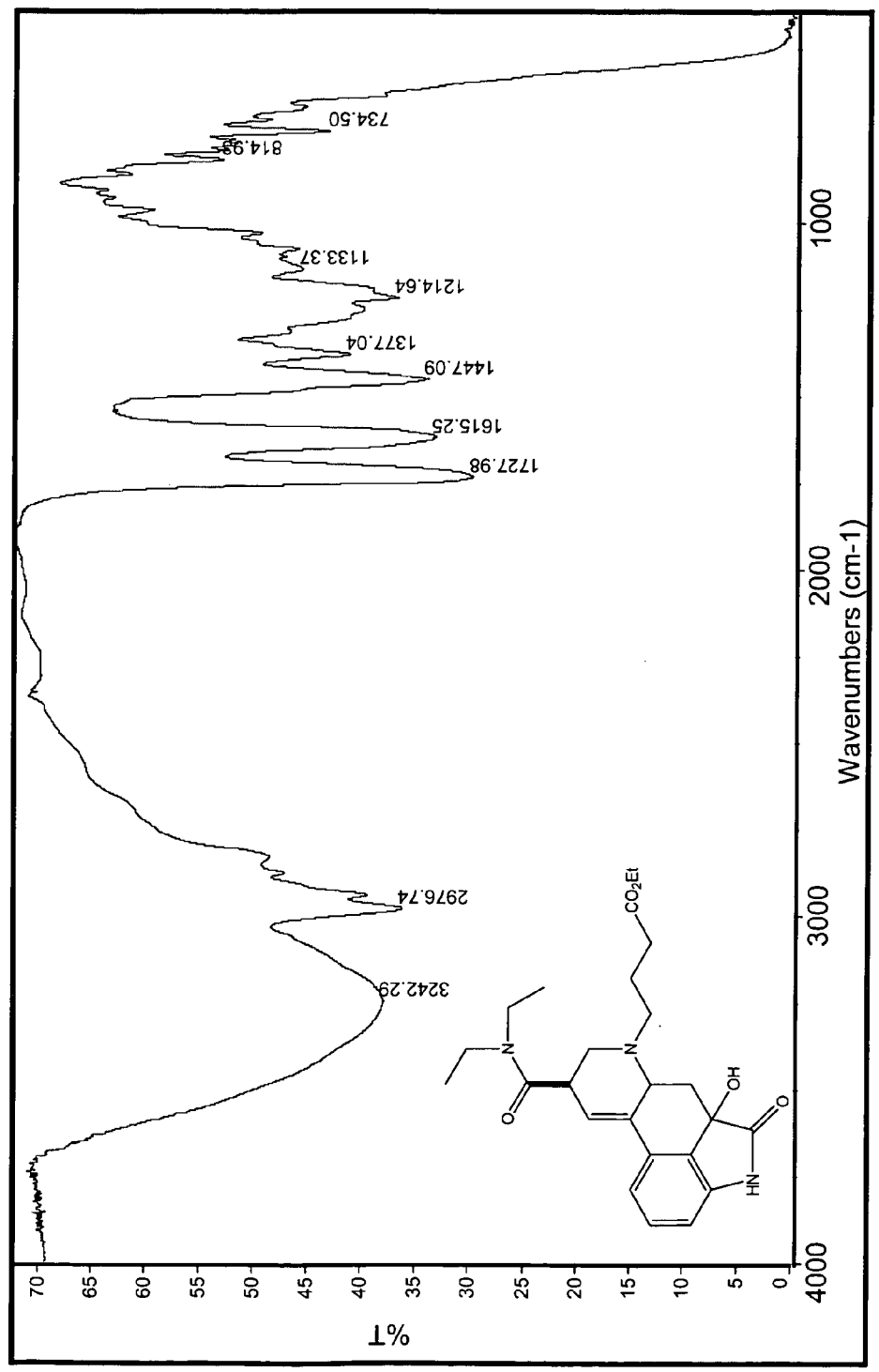
FIG. 12 shows an FT-IR scan of 2-oxo-3-hydroxy-6-(3carboethoxy)propyl-nor-LSD (9).

$\upsilon_{max}$/cm$^{-1}$ 3242.29, 2976.74, 1727.98, 1615.25, 1447.09, 1214.64 (FT-IR: FIG. 12)

Example 10

Synthesis of 2-oxo-3-hydroxy-6-(3-carboxy)propyl-nor-LSD (Hapten B)

To a mixture of 2-oxo-3-hydroxy-6-(3-carboethoxy)propyl-nor-LSD 9 (90 mg, 0.20 mmol) in 3 ml of tetrahydrofuran (THF) and 3 ml of water was added solid potassium hydroxide (22 mg, 0.40 mmol). The reaction was stirred at room temperature for 3 h until the reaction was complete by TLC analysis. The reaction solution was neutralised to pH 7 using 1N HCl and concentrated to dryness under reduced pressure. The residue was dissolved in a 10% methanol in chloroform mixture and the inorganic salts were removed by filtration. Evaporation of the solvents yielded 2-oxo-3-hydroxy-6-(3-carboxy)propyl-nor-LSD (Hapten B), (86 mg, 102%) as a foamy brown solid.

Figure 13:
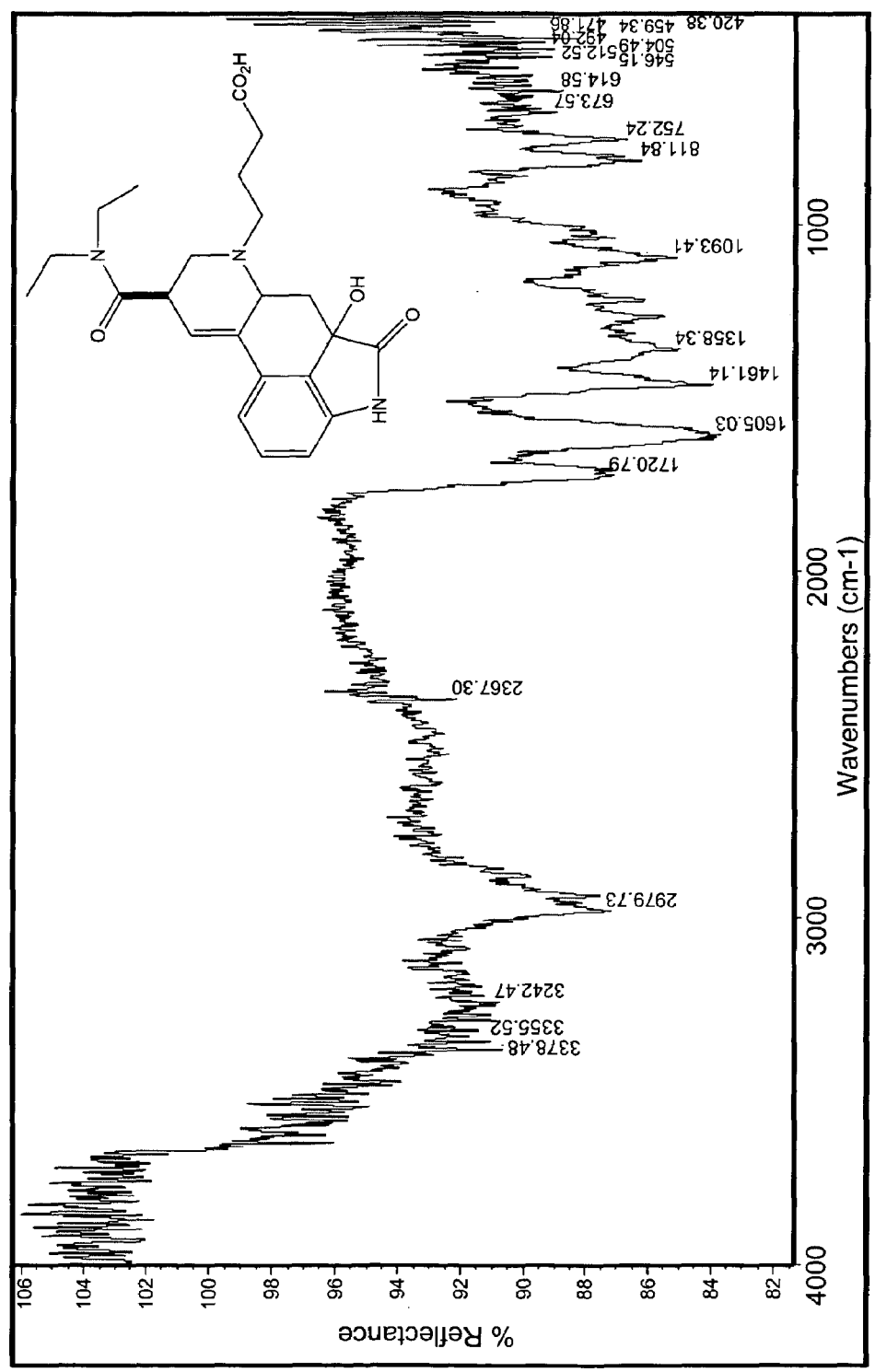
FIG. 13 shows an FT-IR scan of 2-oxo-3-hydroxy-6-(3-carboxy)propyl-nor-LSD (Hapter. B).

$\upsilon_{max}$/cm$^{-1}$ 3242.47, 2979.73, 1720.79, 1605.03 (FT-IR: FIG. 13)

Example 11

Conjugation of 2-oxo-3-hydroxy-6-(3-carboxy)propyl-nor-LSD to BSA (Immunogen B)

To a solution of 2-oxo-3-hydroxy-6-(3-carboxy)propyl-nor-LSD (Hapten B) (32 mg, 0.08 mmol) in 0.5 ml of dimethylforamide (DMF) was added dicyclohexylcarbodiimide (DCC) (18.5 mg, 0.09 mmol) and N-hydroxysuccinimide (NHS) (10.4 mg, 0.09 mmol) and the mixture was stirred at room temperature overnight. The dicyclohexylurea formed was removed by filtration. The solution obtained was added dropwise to a solution of BSA (100 mg) in 6 ml of 0.05M sodium bicarbonate solution (pH 8.5). The mixture was then stirred overnight at 4° C. protected from light. The solution was dialysed against 5L of phosphate buffered saline (PBS) (pH 7.2) at 4° C. for 24 hours (2 changes) and then freeze-dried.

By MALDI-TOF (see FIG. 7 of the accompanying drawings), a major signal was present which indicates an average protonated mass for this sample of m/z 69,699. The signal at m/z 34,862 is consistent with the major component in a doubly-charged form. These data suggest that an average of 8.1 molecules of Hapten B have been conjugated per molecule of BSA.

Example 12

Conjugation of Hapten A to Labelling Agent (Horse Radish Peroxidase (HRP))

10 mg of EDC was dissolved in 800 µl water and immediately added to a solution of the hapten (1 mg) in 200 µl DMF. The resulting solution was mixed gently and then added to a solution of HRP (20 mg) in 1 ml water. After mixing, 5 mg of sulfo-NHS was added and the entire reaction mixture was incubated overnight at room temperature in the dark. The resulting conjugate was purified by passage through two PD10 columns (Pharmacia Biotech), eluted with 20 mM PBS, pH7.2, and then dialysed overnight at 4° C. against 20 mM PBS, pH7.2.

Example 13

Preparation of Antibodies to Immunogen A, Prepared in Example 5.

An aqueous solution of the immunogen prepared in Example 5 was formulated with Freund's Complete Adjuvant (FCA) to form an emulsion consisting of 4 mg/ml inmmunogen in 50% (v/v) FCA. Three sheep were immunized with this emulsion (1° immunisation), 0.25 ml being subcutaneously -injected at each of four sites in the flank of each animal. The next immunisation (Boost 1) contained 2 mg/ml immunogen and subsequent immunizations (boosts 2 to 25) contained 1 mg/ml. All boosts were emulsified in 50% (v/v) Freund's Incomplete Adjuvant (FIA) and administered in the same manner as the 1° immunisation at monthly intervals for 1 year. Blood sampling took place 7 to 14 days after each boost. Each sample was processed to produce antiserum, which was further purified by caprylic acid and ammonium sulfate precipitation to yield an immunoglobulin G (IgG) fraction. The IgG fraction was evaluated by competitive ELISA microtitre plate assay, as described in Example 14 below.

Example 14

Development of a Competitive ELISA for 2-oxo-3-hydroxy-LSD

The wells of an enhanced binding 96 well polystyrene ricrotiter plate were coated with the IgG fraction of the antiserum raised to immunogen A (Example 5) of the present invention, diluted in 10 mM Tris, pH8.5 (125 µl/well). The appropriate antibody coating dilution was determined using standard ELISA chequerboard techniques. The plate was incubated for 2 hours at 37° C., washed 4 times with Tris buffered saline containing Tween 20 (TBST) and tapped dry. Standard solutions of 2-oxo-3-hydroxy-LSD were prepared in TBST at 0, 10, 50, 100, 250, 500, 1000 and 2000 ng/ml and 50 µl of each was added to the appropriate wells (FIG. 4). The conjugate (detection reagent) of the present invention was diluted in Tris buffer (pH7.2) containing EDTA, D-mannitol, sucrose, thimerosal and BSA, the appropriate dilution being determined by standard ELISA chequerboard techniques, and 75 µl was added to the appropriate wells (FIG. 4). The plate was incubated at 37° C. for 2 hours. Excess unbound conjugate was removed by washing 6 times over a 10 minute period with TBST.

125 µl of tetramethylbenzidine (TMB) substrate solution was added to each well of the plate, which was then incubated for 15 to 20 minutes in the dark at room temperature. The reaction was terminated by addition of 125 µl 0.2M H$_2$SO$_4$ to each well. The absorbance was then measured at 450 nm using a microtiter plate reader. The data generated in this assay is presented in Table 1 below.

Example 15

Cross Reactivity of the 2-oxo-3-hydroxy-LSDcompetitive ELISA With LSD and its Metabolites Standard solutions of LSD and its metabolites were prepared in TBST at 0, 10.0, 50.0, 100.0, 250.0, 500.0, 1000 and 2000 ng/ml. Employing each series of standards in the present competitive ELISA, calibration curves were generated and these were used to determine the cross-reactivity of the immunoassays with LSD and its metabolites, cross-reactivity being calculated according to the following formula:

% $CR = IC50_{2\text{-}oxo}/IC50_{LSD} \times 100$ where % CR is the percentage cross-reactivity, IC50$_{2\text{-}oxo}$ is the concentration of 2-oxo-3-hydroxy-LSD that causes 50% displacement of signal and IC50$_{LSD}$ is the concentration of LSD or LSD metabolite that causes 50% displacement of signal.

TABLE 1

Cross-reactivity data generated from a competitive microtiter plate assay for 2-oxo-3-hydroxy-LSD employing antiserum raised to immunogen A (hapten A-BSA) (Example 5) and conjugate A (hapten A-HRP) as detection reagent (Example 12).

| Standard | 2-Oxo-3-Hydroxy-LSD | | Nor LSD | | LSD | |
|---|---|---|---|---|---|---|
| ng/ml | $A_{450}$ | % B/B0 | $A_{450}$ | % B/B0 | $A_{450}$ | % B/B0 |
| 0 | 1.799 | | 1.790 | | 1.805 | |
| 10 | 1.396 | 78.47 | 1.772 | 99.0 | 1.792 | 99.28 |
| 50 | 1.056 | 59.36 | 1.767 | 98.7 | 1.777 | 98.45 |
| 100 | 0.891 | 50.08 | 1.763 | 98.5 | 1.775 | 98.34 |
| 250 | 0.660 | 37.10 | 1.738 | 97.1 | 1.740 | 96.40 |
| 500 | 0.514 | 28.89 | 1.686 | 94.2 | 1.653 | 91.58 |
| 1000 | 0.391 | 21.98 | 1.638 | 91.5 | 1.572 | 87.09 |
| 2000 | 0.318 | 17.88 | 1.552 | 86.7 | 1.453 | 80.50 |
| % CR | | 100 | | <5 | | <5 |

$A_{450}$ = absorbance at 450 nm
B = absorbance at 450 nm at xng/ml standard concentration
B0 = absorbance at 450 nm at 0 ng/ml standard concentration
% CR = percentage cross-reactivity based on specificity to 2-oxo-3-hydroxy LSD It is evident from the results that the present assay is highly specific for 2-oxo-3-hydroxy-LSD and exhibits very low levels of cross-reactivity with LSD and nor LSD.

The invention claimed is:

1. A hapten having the following structural formula:

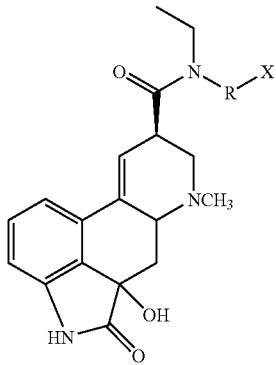

wherein R is a bivalent link and X is a functional group for coupling to an antigenicity-conferring carrier material or to a detectable labeling agent.

2. The hapten of claim 1, wherein R is selected from the group consisting of an alkylene moiety; a cycloalkylene moiety; and an arylene moiety; and X is independently selected from the group consisting of a carboxylic acid or an ester thereof, an aldehyde, a thiocarboxylic acid or an ester thereof, and a halocarboxylic acid or an ester thereof.

3. The hapten of claim 2, wherein X is independently selected from thioacetyl and haloacetyl.

4. The hapten of claim 2, wherein R is a $C_{1-6}$ straight chain, saturated alkylene moiety.

5. The hapten of claim 4, wherein R is a $C_{2-3}$ straight chain, saturated alkylene moiety.

6. The hapten of claim 2, wherein X is carboxylic acid.

7. The hapten of claim 1, the hapten being the following hapten derivative of 2-oxo-3-hydroxy-LSD:

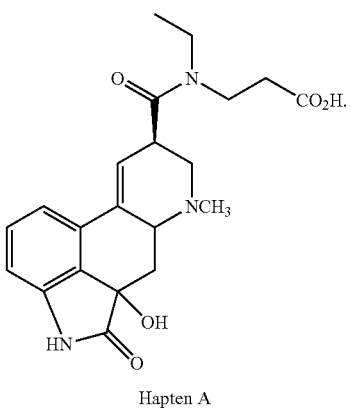

Hapten A

8. The hapten of claim 5, wherein R is a saturated, unsubstituted straight chain alkylene group having 2 carbon atoms.

9. An immunogen having the following structural formula:

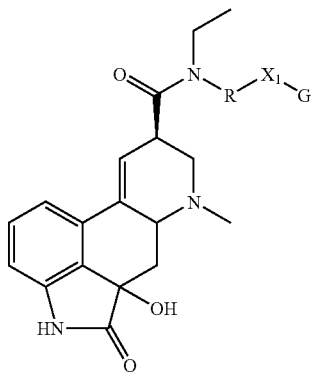

wherein R is a first bivalent group, $X_1$ is a second bivalent group and G is an antigenicity-conferring carrier material.

10. The immunogen of claim 9, wherein R is selected from the group consisting of an alkylene moiety; a cycloalkylene moiety; and an arylene moiety; and $X_1$ is independently selected from the group consisting of a carbonyl (CO), a methylene ($CH_2$), a sulphur atom (S) and a $COCH_2$ group.

11. The immunogen of claim 9, having the following structural formula:

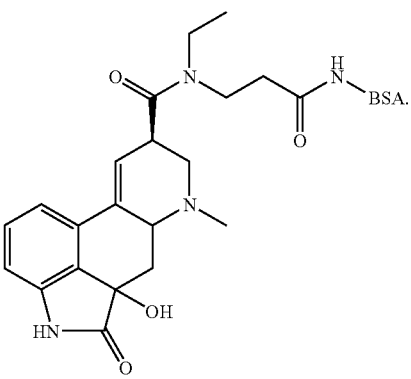

12. An antibody raised against the immunogen of claim 9, wherein the antibody binds at least the 3-hydroxy-2-pyrrolidone structural epitope of 2-oxo-3-hydroxy-LSD and wherein the antibody has a cross-reactivity of less than 25% for LSD and nor LSD, when compared to 100% for 2-oxo-3-hydroxy-LSD.

13. An antibody raised against the immunogen of claim 10, wherein the antibody binds at least the 3-hydroxy-2-pyrrolidone structural epitope of 2-oxo-3-hydroxy-LSD and wherein the antibody has a cross-reactivity of less than 25% for LSD and nor LSD, when compared to 100% for 2-oxo-3-hydroxy-LSD.

14. An antibody raised against the immunogen of claim 11, wherein the antibody binds at least the 3-hydroxy-2-pyrrolidone structural epitope of 2-oxo-3-hydroxy-LSD and wherein the antibody has a cross-reactivity of less than 25% for LSD and nor LSD, when compared to 100% for 2-oxo-3-hydroxy-LSD.

15. A conjugate having the following structural formula:

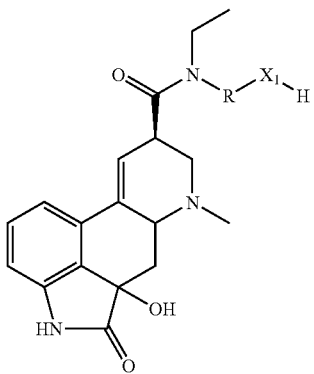

wherein R is a first bivalent group, $X_1$ is a second bivalent group and H that is attached to $X_1$ is a detectable labeling agent.

16. The conjugate of claim 15, wherein R is selected from the group consisting of an alkylene moiety; a cycloalkylene moiety; and an arylene moiety; and $X_1$ is independently selected from the group consisting of a carbonyl (CO), a methylene ($CH_2$) a sulphur atom (S) and a $COCH_2$ group.

17. The conjugate of claim 15, having the following structural formula:

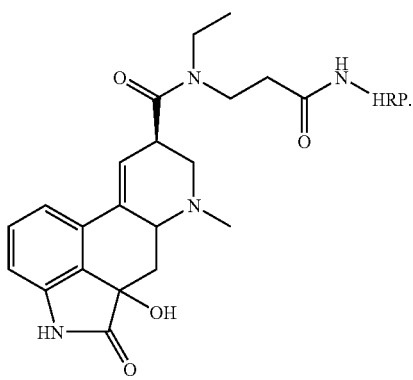

18. The conjugate of claim 15, wherein the labelling agent is selected from the group consisting of an enzyme, a luminescent substance and a radioactive substance.

19. A process of preparing the antibody of claim 12, the process comprising the steps of immunising an animal by repeated administration of the immunogen of claim 9, and collecting the resulting serum from the immunised animal.

20. A process of preparing the antibody of claim 13, the process comprising the steps of immunising an animal by repeated administration of the immunogen of claim 10, and collecting the resulting serum from the immunised animal.

21. A process of preparing the antibody of claim 14, the process comprising the steps of imrnunising an animal by repeated administration of the immunogen of claim 11, and collecting the resulting serum from the immunised animal.

22. A method for detecting or determining 2-oxo-3-hydroxy-LSD in a sample, the method comprising contacting the sample with the conjugate of claim 15 and with at least one antibody of claim 12; detecting or determining bound conjugate; and deducing from a calibration curve the presence of, or the amount of, 2-oxo-3-hydroxy-LSD in the sample.

23. A method for detecting or determining 2-oxo-3-hydroxy-LSD in a sample, the method comprising contacting the sample with at least one conjugate of claim 16 and with at least one antibody of claim 13; detecting or determining bound conjugate; and deducing from a calibration curve the presence of, or the amount of, 2-oxo-3-hydroxy-LSD in the sample.

24. A kit for detecting or determining 2-oxo-3-hydroxy-LSD, the kit comprising at least one conjugate of claim 15; and at least one antibody of claim 12.

25. A kit for detecting or determining 2-oxo-3-hydroxy-LSD, the kit comprising at least one conjugate of claim 16; and at least one antibody of claim 13.

26. An antibody raised against an immunogen of claim 9 having specificity for 2-oxo-3-hydroxy LSD, characterized by having cross reactivity of less than 5% for both LSD and nor LSD, when compared to 100% for 2-oxo-3-hydroxy-LSD.

27. An antibody raised against an immunogen of claim 10 having specificity for 2-oxo-3-hydroxy LSD, characterized by having cross reactivity of less than 5% for both LSD and nor LSD, when compared to 100% for 2-oxo-3-hydroxy-LSD.

28. An antibody raised against an immunogen of claim 11 having specificity for 2-oxo-3-hydroxy LSD, charaterized by having cross reactivity of les than 5% for both LSD and nor LSD, when compared to 100% for 2-oxo-3-hydroxy-LSD.

29. A method for detecting or determining 2-oxo-3-hydroxy-LSD in a sample, the method comprising contacting the sample with conjugate of claim 17, and with at least one antibody of claim 14; detecting or determining bound conjugate; and deducing from a calibration curve the presence of, or the amount of, 2-oxo-3hydroxy-LSD in the sample.

30. A kit for detecting or determining 2-oxo-3-hydroxy-LSD, the kit comprising the conjugate of claim 17; and at least one antibody of claim 14.

\* \* \* \* \*